(12) United States Patent
Johnson et al.

(10) Patent No.: US 11,077,314 B1
(45) Date of Patent: Aug. 3, 2021

(54) SYSTEM AND METHOD FOR TREATING PATIENTS REQUIRING MECHANICAL VENTILATION

(71) Applicant: MULTI RADIANCE MEDICAL, Solon, OH (US)

(72) Inventors: Douglas Johnson, Brownstown, MI (US); Max Kanarsky, Solon, OH (US); Ernesto Leal-Junior, Sao Paulo (BR)

(73) Assignee: MULTI RADIANCE MEDICAL, Solon, OH (US)

( * ) Notice: Subject to any disclaimer, the term of this patent is extended or adjusted under 35 U.S.C. 154(b) by 0 days.

(21) Appl. No.: 17/141,363

(22) Filed: Jan. 5, 2021

Related U.S. Application Data

(60) Provisional application No. 63/017,267, filed on Apr. 29, 2020, provisional application No. 63/035,943, filed on Jun. 8, 2020, provisional application No. 63/115,158, filed on Nov. 18, 2020.

(51) Int. Cl.
*A61N 5/06* (2006.01)
*A61N 2/00* (2006.01)
*A61N 5/067* (2006.01)

(52) U.S. Cl.
CPC ........... *A61N 2/002* (2013.01); *A61N 5/0613* (2013.01); *A61N 2005/067* (2013.01); *A61N 2005/0629* (2013.01); *A61N 2005/0652* (2013.01); *A61N 2005/0659* (2013.01); *A61N 2005/0663* (2013.01)

(58) Field of Classification Search
CPC .................................. A61N 5/06; A61M 16/00
See application file for complete search history.

(56) References Cited

U.S. PATENT DOCUMENTS

| | | | |
|---|---|---|---|
| 6,613,071 B1* | 9/2003 | Fujii ........................ | A61N 5/06 607/91 |
| 2004/0073278 A1* | 4/2004 | Pachys ................. | A61N 5/0601 607/88 |
| 2007/0213792 A1* | 9/2007 | Yaroslavsky ........ | A61N 5/0613 607/100 |
| 2013/0324788 A1* | 12/2013 | Holley .............. | A61M 16/0633 600/28 |
| 2018/0043162 A1* | 2/2018 | Canning .............. | A61N 1/3601 |
| 2018/0368762 A1* | 12/2018 | Pirtini Cetingul ..... | A61G 11/00 |
| 2019/0254901 A1* | 8/2019 | Fernandes ............. | A61F 5/4407 |

FOREIGN PATENT DOCUMENTS

CN 110141750 A * 8/2019

* cited by examiner

*Primary Examiner* — Lynsey C Eiseman
(74) *Attorney, Agent, or Firm* — Tarolli, Sundheim, Covell & Tummino LLP

(57) ABSTRACT

Respiratory function can be preserved in patients requiring mechanical ventilation (MV), such as patients with severe COVID-19, using a photoceutical applied by a photoceutical medical device (including at least one super pulsed laser to provide superpulsed light of a first wavelength, at least two non-coherent light sources to provide light of a second wavelength, and at least two other non-coherent light sources to provide light of a third wavelength) to at least one inspiratory muscle. The photoceutical includes a combination of superpulsed light of the first wavelength, light of the second wavelength, and light of the third wavelength. At least two sites on the body of the patient can be selected and the photoceutical can be delivered: at one of the sites for a first time period; and at another of the sites for a second time period.

14 Claims, 15 Drawing Sheets

SYSTEM AND METHOD FOR TREATING PATIENTS REQUIRING MECHANICAL VENTILATION

CROSS-REFERENCE TO RELATED APPLICATIONS

This application claims the benefit of U.S. Provisional Application No. 63/017,267, filed Apr. 29, 2020, entitled "PHOTOBIOMODULATION THERAPY TO INCREASE HEALTH STATUS OF COVID-19 PATIENTS"; U.S. Provisional Application No. 63/035,943, filed Jun. 8, 2020, entitled "PHOTOBIOMODULATION THERAPY TO INCREASE HEALTH STATUS OF COVID-19 PATIENTS"; and U.S. Provisional Application No. 63/115,158, filed Nov. 18, 2020, entitled "PHOTOBIOMODULATION THERAPY TO INCREASE HEALTH STATUS OF COVID-19 PATIENTS". These provisional applications are hereby incorporated by reference in their entirety for all purposes.

TECHNICAL FIELD

The present disclosure relates generally to treating patients requiring mechanical ventilation (MV) and, more specifically, to systems and methods for treating patients, such as patients with severe COVID-19, requiring MV with a photoceutical that includes combined (1) infrared super pulsed laser light, (2) infrared light from an infrared light emitting diode (IRED), (3) red light from a light emitting diode (LED) light, and, in some instances, (4) a static magnetic field.

BACKGROUND

Coronaviruses are a large family of viruses which may cause illness in animals or humans. In humans, several coronaviruses are known to cause respiratory infections ranging from the common cold to more severe diseases, such as Middle East Respiratory Syndrome (MERS), Severe Acute Respiratory Syndrome (SARS), and the like. The most recently discovered coronavirus causes coronavirus disease 2019 (COVID-19). Patients with severe COVID-19 often suffer from acute respiratory distress syndrome (ARDS), a life-threatening condition where breathing becomes difficult and oxygen cannot get into the body due to fluid building up inside the alveoli (tiny air sacs of the lungs) and break down of surfactant, a foamy substance that keeps the lungs fully expanded so that a person can breathe. These changes prevent the lungs from filling properly with air and moving enough oxygen into the bloodstream and throughout the body. Without proper oxygenation of tissues, metabolic processes cannot function efficiently, and cellular functions will falter. The first symptom of ARDS is usually shortness of breath, as well as low blood oxygen, rapid breathing, and clicking, bubbling, or rattling sounds in the lungs when breathing.

Respiratory failure due to hypoxemia is one of the most prominent complications in patients with ARDS. Treatment of respiratory failure can include providing supplemental oxygen or lung protective mechanical ventilation (MV) and prone positioning. MV requires intubation with an endotracheal tube may be for an extended duration in an Intensive Care Unit (ICU). Prolonged MV may result in ventilator-induced diaphragm dysfunction (VIDD), due to the suppression or elimination of spontaneous ventilatory muscle activity. As many as 80 percent of patients surviving respiratory failure after receiving MV in the ICU experience new or worsened physical, cognitive and/or mental health impairments that persist beyond hospital discharge, collectively known as the post-intensive care syndrome. In addition, the strength of the respiratory muscles may also be reduced, which makes it difficult to wean patients from MV successfully. Along with MV, these patients often require deep sedation, neuromuscular blockade, and associated immobility, which increase the risk of physical impairments. Serious or life-threatening complications include organ damage or organ failure and death.

SUMMARY

The present disclosure relates to treating patients requiring mechanical ventilation (MV) with a photoceutical that includes a light signal of combined (1) infrared super pulsed laser light, (2) infrared light from an infrared light emitting diode (IRED), (3) red light from a light emitting diode (LED) light, and, in some instances, (4) a static magnetic field. The photoceutical can be delivered to points on the patient's body (e.g., abdomen, chest, neck, etc.) to reach the primary inspiratory muscles by a photoceutical delivery device. In some instances, the patient requiring mechanical ventilation can be exhibiting severe COVID-19.

In one aspect, the present disclosure can include a method for preserving a respiratory function within the body of the patient requiring mechanical ventilation while on mechanical ventilation. At least two sites on a body of a patient requiring mechanical ventilation can be selected for delivery of a light signal to at least one primary inspiratory muscle of the patient requiring mechanical ventilation by a photoceutical medical device (also referred to as a photoceutical delivery device). The photoceutical medical device can include at least one super pulsed laser to provide super-pulsed light of a first wavelength, at least two non-coherent light sources to provide light of a second wavelength, and at least two other non-coherent light sources to provide light of a third wavelength, such that the light signal comprises superpulsed light of the first wavelength, light of the second wavelength, and light of the third wavelength. The light signal can be delivered to the at least one primary inspiratory muscle of the patient requiring mechanical ventilation by the photoceutical medical device at one of the at least two sites for a first time period from a first start time to a first end time; and after the first end time, delivering the light signal to the at least one primary inspiratory muscle of the patient requiring mechanical ventilation by the photoceutical medical device at another of the at least two sites for a second time period from a second start time to a second end time.

In another aspect, the present disclosure can include a photoceutical medical device that can act as the photoceutical delivery device. The device can include a circuit board comprising: a plurality of light sources to provide a light signal and at least two magnets to provide a magnetic signal. The plurality of light sources can include at least one super pulsed laser to provide superpulsed light of a first wavelength, at least two non-coherent light sources to provide light of a second wavelength, at least two other non-coherent light sources to provide light of a third wavelength, such that the light signal includes the superpulsed light of the first wavelength, the light of the second wavelength, and the light of the third wavelength. The light signal and the magnetic signal are delivered to at least two sites on a body of a patient requiring mechanical ventilation to deliver the light signal and the magnetic signal to at least one primary inspiratory muscle of the patient requiring mechanical ventilation. The device can also include a power source (which may be at least partially on or in communication with the circuit board).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
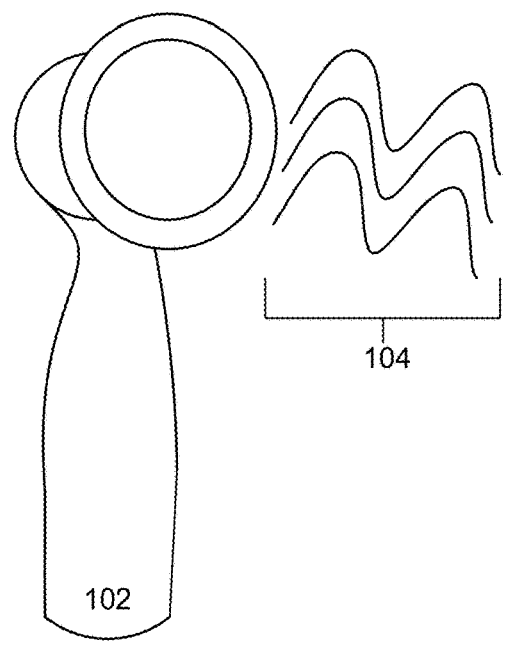
FIG. 1 is a diagram showing an example of a system including a photoceutical medical device that delivers a photoceutical to at least one predefined location on the body of a patient requiring mechanical ventilation (MV) in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "mechanical ventilation" refers to a form of life support that uses a mechanical ventilator (also referred to as a respirator, a breathing machine, or the like) to help a patient breathe by taking over the work of breathing when a patient cannot breathe on their own. The patient is connected to the mechanical ventilator with a hollow endotracheal tube that goes in their mouth and down into their trachea to create an artificial airway.

As used herein, the term "intubation" refers to the process of inserting an endotracheal tube through the mouth and into the trachea. This is done so that a patient can be placed on a mechanical ventilator to assist with breathing, for example.

As used herein, the term "photoceutical" refers to a light signal (or a light signal and magnetic signal) used to change a function of at least a portion of a patient's body (e.g., by photobiomodulation to induce a phototherapeutic response using a drug-free, non-invasive treatment procedure). For example, the light signal of the photoceutical may include a combination of a plurality of light signals from a plurality of light sources, each of the plurality of light signals may have a different wavelength, frequency, or other property. The combination of the different properties (like wavelength, for example) can create a synergistic effect.

As used herein, the terms "photoceutical delivery device", "photoceutical medical device", "photoceutical device", and the like, refer to a device configured to apply the photoceutical as a therapeutic agent. For example, the photoceutical delivery device can house the plurality of light sources (and, in some instances, the magnets) to deliver the pharmaceutical. The light sources can include one or more super pulsed lasers, one or more light emitting diodes, one or more infrared light emitting diodes, or the like.

As used herein, the term "super pulsed laser" refers to a light source that produces a wavelength of light at a high peak power for a very brief duration. Even though the pulse peaks at a high power level, there are no thermal effects in the tissue. The peak power is high compared to the average output power. By using a super pulsed laser, one is able to more effectively deliver higher densities of light energy into the tissue without associated deleterious thermal effects.

As used herein, the term "incline" refers to a deviation from vertical or horizontal by a certain slope at a particular angle.

As used herein, the term "circuit board" refers to a mechanism to mechanically support and electrically connect electrical components (like light delivery devices) using conductive tracks, pads, and other features etched from one or more sheet layers of a conductive material (like copper) laminated onto and/or between sheet layers of a non-conductive substrate. The circuit board can be rigid and/or flexible. An example of a circuit board can include a printed circuit board.

As used herein, the term "sufficient" refers to an amount adequate enough to satisfy a condition.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc. The patient can require mechanical ventilation. In some instances, the patient can be suffering from severe COVID-19.

II. Overview

Patients suffering from acute respiratory distress syndrome (ARDS), such as patients with severe COVID-19, cannot get oxygen cannot get into their body due to their lungs not filling properly with air due to fluid building up inside the alveoli and break down of surfactant. This prevents adequate amounts of oxygen from moving into the bloodstream and throughout the body, eventually causing respiratory failure due to hypoxemia. One treatment of respiratory failure can include life supportive mechanical ventilation (MV) with deep sedation, neuromuscular blockade, and associated immobility. Prolonged mechanical ventilation may result in diaphragm dysfunction and the weakening of muscles needed for breathing, such as the diaphragm, intercostals, and accessory muscles, due to the suppression or elimination of spontaneous ventilatory muscle activity.

The diaphragm is a thin dome-shaped muscle situated in the superior aspect of the abdominal cavity below the ribs and the intercostal muscles separating the abdominal cavity from the thoracic cavity. The diaphragm is the major muscle responsible for breathing, working like a piston to expand the chest cavity. During inhalation, the diaphragm contracts, so that its center moves caudally (downward) and its edges move cranially (upward). This compresses the abdominal cavity, raises the ribs upward and outward and thus expands the thoracic cavity. This expansion creates a vacuum that draws air into the lungs. When the diaphragm relaxes, elastic recoil of the thoracic wall causes the thoracic cavity to contract, forcing air out of the lungs, and returning to its dome-shape. Intercostal muscles participate in both inspiration and expiration. The thoracic accessory muscles (scalenes, sternocleidomastoids, pectoralis minor, and erector spinae) all elevate the ribs and facilitate inspiration. The abdominal accessory muscles (rectus abdominis, transverse abdominis, and the obliques) facilitate expiration. The term accessory muscles refers to those muscles that assist, but do not play a primary role, in breathing. Use of these while at rest is often interpreted as a sign of respiratory distress.

Surviving respiratory failure patients after receiving MV in the ICU often experience new or worsened physical, cognitive and/or mental health impairments that persist beyond hospital discharge, collectively known as the post-intensive care syndrome. In addition, the strength of the respiratory muscles may also be reduced, which makes it difficult to wean patients from MV successfully. Serious or life-threatening complications include organ damage or organ failure and death. Applying a photoceutical to at least two spots on a patient's body (e.g., delivering the photoceutical to the diaphragm and/or the neck) can preserve respiratory function, improving one or more of ventilation parameters, blood oxygenation, tissue oxygenation, and immune response, decreasing at least one of inflammation and length of intensive care unit (ICU) stay, minimizing symptoms of post-intensive care syndrome, reduced length of intubation, reduced length of mechanical ventilation, reduced acute respiratory distress syndrome, maintained muscle morphology, maintained muscle function, reduced infection, reduced inflammation, reduced sepsis, and/or decreased length of hospitalization. Accordingly, the present disclosure relates to systems and methods treating of patients, such as patients with severe COVID-19, requiring MV with the photoceutical. The photoceutical can include a light signal made up of superpulsed light of a first wavelength, light of a second wavelength, and light of a third wavelength (two of the wavelengths can be substantially matched and one wavelength different). For instance, the photoceutical can include application of the light signal to each of the at least two spots for a time period. The photoceutical can be delivered by a photoceutical medical device that includes at least one super pulsed laser to provide superpulsed light of the first wavelength, at least two non-coherent light sources to provide light of the second wavelength, and at least two other non-coherent light sources to provide light of a third wavelength (and may, additionally, include one or more magnets to provide a magnetic signal).

III. Photobiomodulation Therapy (PBMT)

Applying the photoceutical to a patient is a drug-free and non-invasive photobiomodulation therapy (PBMT) that can be used to treat patients requiring mechanical ventilation (MV), such as patients with severe COVID-19 suffering from acute respiratory distress syndrome (ARDS) or respiratory failure. Prolonged MV may result in diaphragm dysfunction and the weakening of muscles needed for breathing, the primary inspiratory muscles including the diaphragm, intercostals, and accessory muscles, due to the suppression or elimination of spontaneous ventilatory muscle activity. Application of a dose of the photoceutical to a patient being mechanically ventilated can induce a phototherapeutic response that can reduce the dysfunction and weakening of muscles needed for breathing. For example, application of the photoceutical can reduce atrophy of the primary inspiratory muscles (e.g., the diaphragm, the sternocleidomastoid muscles, and the scalene muscles). By reducing the atrophy of the primary inspiratory muscles, the health status of such patients can be improved, for example by preserving respiratory function by minimizing muscle weakness and fatigue in the primary inspiratory muscles. The preserved respiratory function can cause improved ventilation parameters, improved blood oxygenation, improved tissue oxygenation, improved immune response and/or overall function of the immune system, decreased inflammation, minimized symptoms of post-intensive care syndrome, decreased length of intensive care unit (ICU) stay, reduced length of intubation, reduced length of mechanical ventilation, reduced acute respiratory distress syndrome, maintained muscle morphology, maintained muscle function, reduced infection, reduced inflammation, reduced sepsis, and/or decreased length of hospitalization.

The light signal of the photoceutical may include a combination of a plurality of light signals from a plurality of light sources, each of the plurality of light signals may have a different wavelength, frequency, or other property. The combination of the different properties (like wavelength, for example) can create a synergistic effect. The light signal includes a combination of a superpulsed light of a first wavelength (850 nm-950 nm), light of a second wavelength (800 nm-900 nm), and light of a third wavelength (580 nm-800 nm). In some instances, the light signal includes a magnetic signal (or magnetic field). A dose of the light signal can be applied for a time period from a first time to a second time, wherein the time periods is between 30 seconds to 300 seconds to each predefined site on the patient's body for treatment of the diaphragm, the sternocleidomastoid muscle(s), and/or the scalene muscle(s).

The light of PBMT has been shown to have a modulatory effect on muscle cells based on the principle that certain molecules in living systems absorb photons and trigger signalling pathways in response to light. When a photon of light is absorbed by a chromophore in a cell, an electron in the chromophore can become excited and jump from a low-energy orbit to a higher-energy orbit. This stored energy then can be used by the living system to perform various cellular tasks, such as cellular metabolism, microcirculation, promoting oxygen availability, and modulation of the inflammatory process, attributable to the acceleration of the electron transport chain and reestablishment of oxidative phosphorylation. While not wishing to be bound by theory, there is strong evidence to suggest that one of the basics of PBMT is the acceleration of electron transfer by electromagnetic radiation in the visible and near infrared region of the spectrum, via the modulation of cytochrome c-oxidase ("CCO") activity in muscle cells. CCO is the primary photo acceptor of visible to near infrared light energy and is the enzyme responsible for catalysing oxygen consumption in cellular respiration and for the production of nitric oxide under hypoxic conditions. High-energy electrons are passed from electron carriers through a series of trans-membrane complexes (including CCO) to the final electron acceptor, generating a proton gradient that is used to produce adenosine triphosphate (ATP). The application of light directly results in ATP production and electron transport. In short, the application of PBMT can increase ATP production, down-regulate cellular respiration modulated by NO, and promotes the metabolism of oxygen, while increasing the production of reactive oxygen species (ROS).

IV. Systems

As shown in FIG. 1, one aspect of the present disclosure can include a system including a photoceutical medical device 102 that delivers a photoceutical 104. The system can be used to deliver the photoceutical 104 to at least one predefined location on the body of a patient requiring mechanical ventilation (MV), such as a severe COVID-19 patient suffering from acute respiratory distress syndrome (ARDS) and/or respiratory failure. Patients on prolonged mechanical ventilation may experience consequences of the suppression or elimination of spontaneous ventilatory muscle activity, such as dysfunction of the diaphragm, the primary muscle used for breathing. In addition to other complications, it may be difficult to wean these patients from MV because the strength of the respiratory muscles (the diaphragm and other muscles needed for breathing) may also be reduced. In fact, applying the photoceutical 104 to at least two sites on a patient's body (e.g., delivering the photoceutical to the diaphragm and/or the neck) can improve the function and strength of the muscles. Improving the function and strength of the muscles can preserve respiratory function, improve one or more of ventilation parameters, blood oxygenation, tissue oxygenation, and immune response, decrease at least one of inflammation and length of intensive care unit (ICU) stay, minimize symptoms of post-intensive care syndrome, reduce length of intubation, reduce length of mechanical ventilation, reduce acute respiratory distress syndrome, maintain muscle morphology, maintain muscle function, reduce infection, reduce inflammation, reduce sepsis, and/or decrease length of hospitalization. In some instances, the at least two sites on the patient's body can include at least two sites targeting the patient's diaphragm and at least one site on the patient's neck (targeting at least the sternocleidomastoid muscle(s), and/or the scalene muscle(s)). In other instances, the at least two sites on a patient's body can include from 1 to 3 sites (bilaterally) targeting the patient's diaphragm and from 0-1 site (bilaterally) targeting the patient's neck (targeting at least the sternocleidomastoid muscle(s), and/or the scalene muscle(s)).

The photoceutical 104 can include a light signal made up of a combination of different lights from different sources. For example, the different lights can be coherent or incoherent and have different wavelengths, frequencies, energies, energy density delivered, and the like. In one instance, the light signal can include superpulsed light of a first wavelength, light of a second wavelength, and light of a third wavelength (two of the wavelengths can be substantially matched and one wavelength different). For example, the first wavelength can be between 850 nm and 950 nm, the second wavelength can be between 800 nm and 900 nm, and the third wavelength can be between 580 nm and 800 nm. In some instances, the photoceutical 104 can also include a magnetic signal (e.g., from one or more magnetic sources, which can be permanent magnets, with a magnetism provided by each magnetic source of from 0.01 mT-100 mT). The photoceutical 104 can deliver a dose of energy to each of the at least one predefined location on the body of a patient. The dose of energy can be, for example, 31.5 J. The photoceutical 104 can be applied to each predefined site for a time period from a first time to a second time, wherein the time periods is between 30 seconds to 300 seconds for treatment of the diaphragm, the sternocleidomastoid muscle(s), and/or the scalene muscle(s).

The photoceutical 104 can be delivered to at least one predefined location on the body of the patient requiring MV by the photoceutical medical device 102. The photoceutical medical device 102 can include at least one super pulsed laser to provide superpulsed light of the first wavelength, at least two non-coherent light sources to provide light of the second wavelength, and at least two other non-coherent light sources to provide light of a third wavelength. The photoceutical medical device 102 can also include at least two magnetic sources to provide the magnetic field. However, in some instances, the photoceutical medical device 102 can include at least four super pulsed lasers to provide superpulsed light of the first wavelength, at least eight non-coherent light sources to provide light of the second wavelength, and at least eight other non-coherent light sources to provide light of a third wavelength. In these instances, the photoceutical medical device 102 can also include at least eight magnetic sources to provide the magnetic field.

Figure 2:
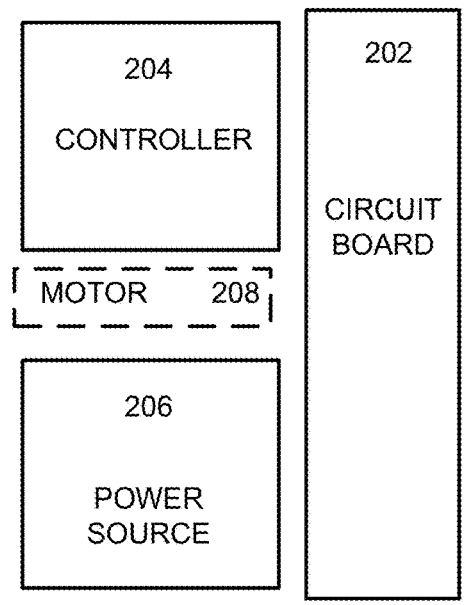
FIG. 2 is a diagram showing an example interior of the photoceutical medical device of FIG. 1.

The photoceutical medical device 102 can be of different shapes and sizes so long as the photoceutical medical device is shaped and sized to deliver the photoceutical 104 to the one or more predefined sites on the patient. As examples, the photoceutical medical device 102 may be configured to be held against (as illustrated) and/or placed onto one or more treatment sites for delivery of the photoceutical 104. While the photoceutical 104 can be emitted from a one or more circular emitters (as shown in FIG. 1), the emitters need not be circular. For example, the emitters can be one or more diamonds, crosses, squares, rectangles, or the like. Components of the photoceutical medical device 102 that facilitate generation and delivery of the photoceutical 104 are shown in FIG. 2. It should be understood that the photoceutical medical device 102 can include additional components to facilitate the generation and delivery of the photoceutical 104 (e.g., one or more lenses).

Figure 6:
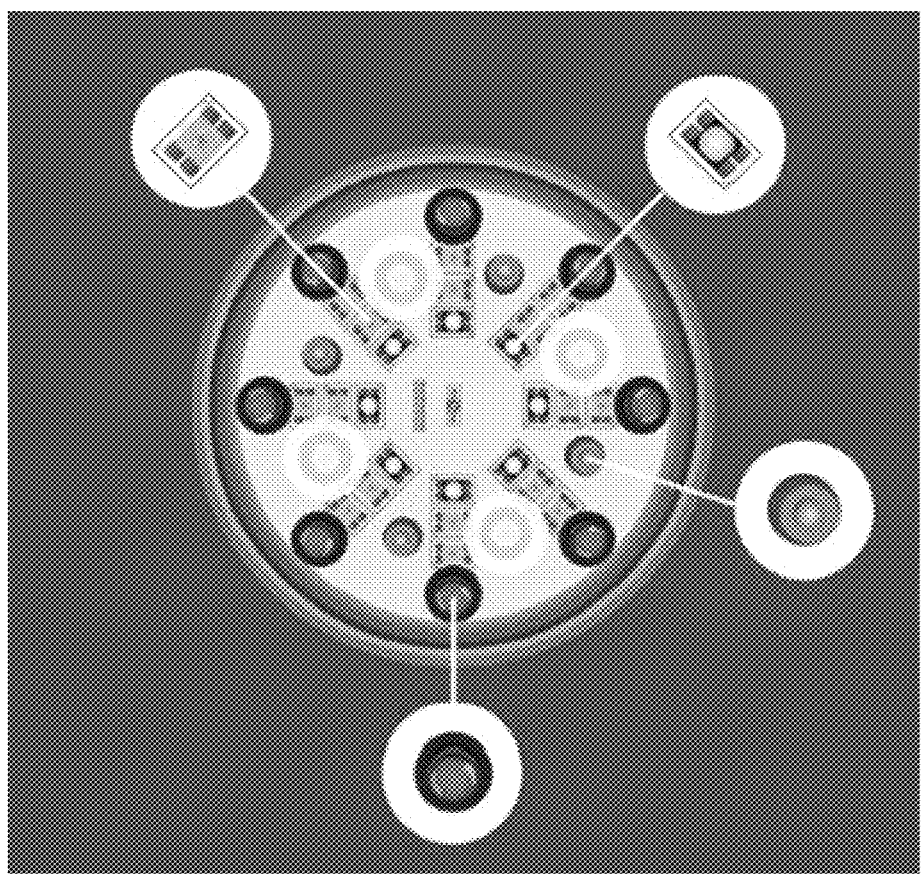
FIG. 6 is an example photograph with components enlarged of the light delivery surface of the MR5Active Pro LaserShower device.

The photoceutical medical device 102 can include a circuit board 202 (also referred to as a printed circuit board), which can hold the light sources (which can be positioned in a manner for delivery, as shown, for example, in FIG. 6, but this is not the exclusive manner of delivery). Each light source can deliver a unique signal from a unique position, and these unique signals are combined to form the photoceutical. The light sources can include one or more superpulsed lasers, one or more red light emitting diodes (LEDs), and one or more infrared light emitting diodes (IRED). In some instances, the circuit board can include one or more magnetic sources.

The circuit board can be, in some instances, a flexible circuit board, and in other instances a rigid circuit board. The circuit board 202 can be connected to a controller 204 and a power source 206. The controller 204 can be configured to receive an input, for example an external input from a user, a memory storing instructions, and a processor to execute the instructions. The instructions can include programming for delivery of the photoceutical 204, including the duration of the delivery of the photoceutical, the start time, the stop time, the total power, based on the power delivered by each source (the types of light sources and, in some instances, the magnetic sources), and the like. Although the controller 204 can be controlled by an input, in some instances, the controller 204 can be preprogrammed such that only a start or stop button is required. In some instances, at least a portion of the controller can be external to the photoceutical medical device 102. The power source 206 can provide line power and/or battery power to power at least a portion of the photoceutical delivery device 102 (e.g., the controller 204, which can deliver power to the circuit board 202) and can include additional circuitry related to power delivery.

Figure 3:
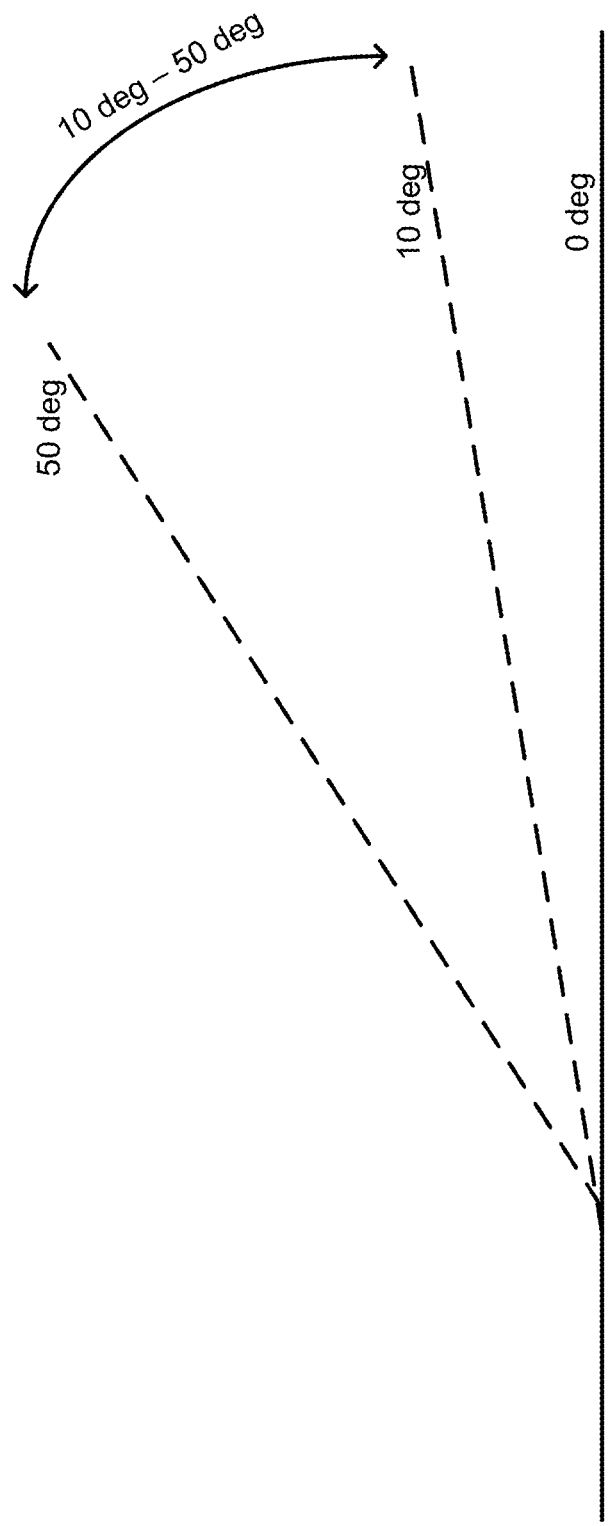
FIG. 3 is a diagram showing an example variable incline of the circuit board of the photoceutical medical device of FIG. 2.

In some instances, the photoceutical medical device 102 can include a motor 208 to incline the circuit board 202 for delivery to at least one of the predefined sites on the patient's body. However, in other instances, the circuit board 202 can be angled manually by angling the photoceutical medical device 102. As shown in FIG. 3, in some instances, like when the photoceutical 104 is delivered to the neck of the patient, the circuit board need not be on an incline (0 deg as shown in FIG. 3). However, when the photoceutical 104 is delivered to one of the sites on the patient's abdomen, the circuit board can be inclined from 10 degrees to 50 degrees (10 deg-50 deg as shown in FIG. 3) to facilitate delivery of the photoceutical 104 to the diaphragm. The incline may be different (but between 10 degrees and 50 degrees) for different sites on the patient's abdomen; in these instances, the photoceutical medical device 102 can be placed at an edge of costal cartilage and angled to facilitate delivery of the photoceutical 104 to the diaphragm. The motor 208 can be programmed to move the circuit board to a specific include to deliver the photoceutical 204 based on the anatomical location of the predefined site.

V. Methods

Figure 4:
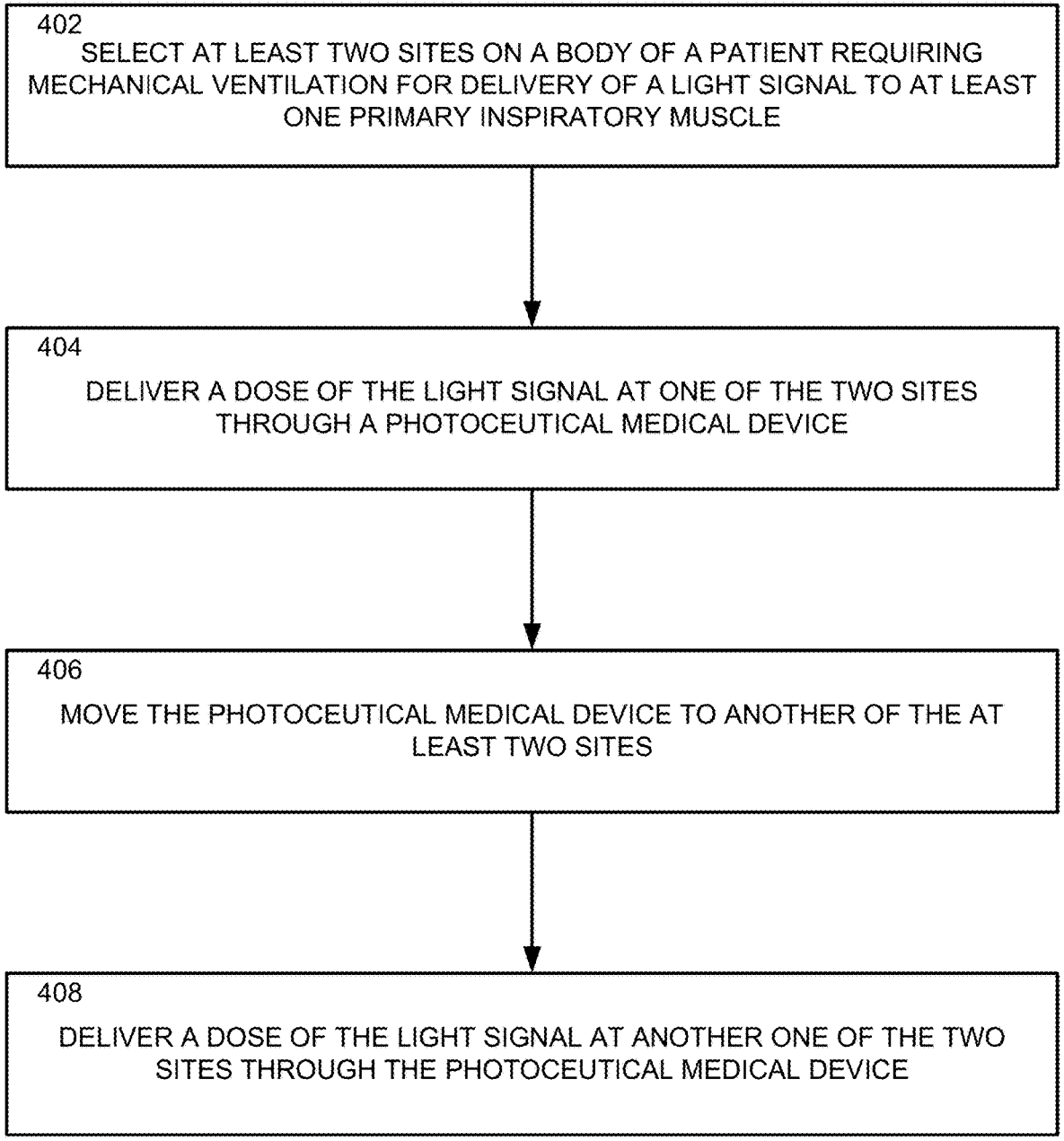
FIG. 4 is a process flow diagram of an example method for delivering a photoceutical to a patient requiring MV in accordance with another aspect of the present disclosure.

Another aspect of the present disclosure can include a method 400, as shown in FIG. 4, for treating a patient with photoceutical medical device to preserve a respiratory function of a patient on mechanical ventilation. The method 400 can be executed by hardware—for example, at least a portion of the system 102 shown in FIGS. 1 and 2 and described above. The method 400 is illustrated as process flow diagrams with flowchart illustrations. For purposes of simplicity, the method 400 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 400. Additionally, one or more elements that implement the method 400, such as the photoceutical delivery device 102 or the controller 204 of FIG. 2, may include a non-transitory memory and one or more processors that can facilitate the configuration and generation of the light of the photoceutical.

At step 402, at least two sites on a body of a patient who requires mechanical ventilation are selected for delivery of a light signal to at least one primary inspiratory muscle. The patient who requires mechanical ventilation can be a patient suffering from severe COVID-19. The patient may also require intubation. For example, the primary inspiratory muscles can include the diaphragm, the sternocleidomastoid muscles, and the scalene muscles. The at least two sites are selected based on the muscle the photoceutical is being delivered to. In many instances, the at least two sites are predetermined.

For example, the at least two sites can be on an abdomen of the patient to target the patient's diaphragm. The at least two sites can be selected so that the light signal can be delivered under the ribcage of the patient at the left dome or the right dome of the patient's diaphragm. In another aspect, the selecting at least two sites can include selecting between two and six sites on the abdomen of the patient. In another example, at least one of the at least two sites can be on the neck of the patient. The sites on the neck can be additional to the sites on the abdomen or can be without the sites on the abdomen. However, as an example, the selecting can include selecting at least six sites on the abdomen of the patient and at least two additional sites on the neck of the patient. The sites on the abdomen are selected so the light signal can be delivered to the patient's diaphragm. The sites on the patient's neck are selected so the light signal can be delivered to the patient's sternocleidomastoid and/or scalene muscles.

At step 404 a dose of the light signal is delivered at one of the at least two sites through a photoceutical medical device 102. The photoceutical medical device 102 can be a handheld device, as shown in FIG. 1, or it can be applied to the patient's body independently (without being handheld). The photoceutical device comprises at least one super pulsed laser that can provide superpulsed light of a first wavelength, at least two non-coherent light sources that can provide light of a second wavelength, and at least two other non-coherent light sources to provide light of a third wavelength. The light signal delivered by the photoceutical medical device can include a combination of superpulsed light of the first wavelength, light of the second wavelength, and light of the third wavelength. For example, the first wavelength can be between 850 nm and 950 nm, the second wavelength can be between 800 nm and 900 nm, and the third wavelength can be between 580 and 800 nm. The photoceutical medical device can also comprise at least two magnetic sources to provide a magnetic signal. The magnetic sources can be, for example, one or more of: a permanent magnet, a temporary magnet, and an electromagnet.

In another aspect the photoceutical medical device can comprise at least four super pulsed lasers, at least eight light sources, at least eight other light sources, and at least eight magnetic sources. The at least four super pulsed lasers can each provide the superpulsed light of the first wavelength. The at least eight light sources can each provide the light of the second wavelength. The at least eight other light sources can each provide the light of the third wavelength. The at least eight magnetic sources can provide a magnetic signal.

The dose of the light signal delivered to the at least one primary inspiratory muscle of the patient by the photoceutical medical device at one of the at least two sites can be delivered for a first time period from a first start to a first end time. The first time period can be between 30 seconds and 300 seconds. The dose delivered for the first time period can be 31.5 J. When at least one of the at least two sites are on an abdomen of the patient to target the diaphragm the delivering the light signal can further include angling at least a portion of the photoceutical medical device (e.g., at least the circuit board) so that the light signal enters the body of the patient at an angle from 10 degrees to 50 degrees to reach the diaphragm of the patient. However, the photoceutical medical device need not be inclined to deliver the photoceutical to any sites being on the neck of the patient.

At step 406 the photoceutical medical device 102 is moved to another of the at least two site and, at step 408, a dose of the light signal is delivered at another one of the at least two sites through the photoceutical medical device. The photoceutical medical device can be moved to the another of the at least two sites after the first end time and the other dose of the light signal can be delivered at the another of the at least two sites for a second time period from a second start time to a second end time. The second time period can be between 30 seconds and 300 seconds. The other dose delivered for the second time period can be 31.5 J.

In other aspects, the light signal can be delivered (via the method described above) to the selected at least six sites on the body of the patient and to the selected at least six sites on the abdomen of the patient and the at least two additional sites on the neck of the patient. These delivering steps can include moving and delivering a dose of the light signal at each selected site. The delivering steps can be completed sequentially by placing the photoceutical medical device at an edge of costal cartilage while avoiding the xiphoid process at one or more of the at least six sites. Each dose can be 31.5 J and each dose can be delivered for a time period that can be between 30 seconds and 300 seconds.

The light signal is applied to the patient to preserve a respiratory function within the patient's body when the patient is on mechanical ventilation by preserving the strength and functionality of one or more muscles used in breathing. Preserving respiratory function of a patient on mechanical ventilation can cause, for example: improved ventilation parameters, improved blood oxygenation, improved tissue oxygenation, improved immune response, decreased inflammation, minimized symptoms of post-intensive care syndrome, decreased length of intensive care unit (ICU) stay, reduced length of intubation, reduced length of mechanical ventilation, reduced acute respiratory distress syndrome, maintained muscle morphology, maintained muscle function, reduced infection, reduced inflammation, reduced sepsis, and/or decreased length of hospitalization.

VI. Experimental

Figure 5:
FIG. 5 is a photograph of a MR5Active Pro LaserShower device.

This Experiment shows a randomized triple-blinded placebo-controlled trial (Performed in Brazil under the watch of the Ministry of Health) of the photoceutical including the application of a specific combination of infrared super pulsed laser (SPL) light, infrared IRED light, red LED light, and a static magnetic field (parameters shown in Table 1) by a photoceutical medical device (MR5Active Pro LaserShower, 250 Hz frequency; MultiRadiance Medical of Solon, Ohio; shown in FIGS. 5 and 6).

TABLE 1

Parameters for specific application of the photoceutical.

| Wavelength | Source | Number of Sources | Power/each | Total Power |
|---|---|---|---|---|
| 905 nm | SPL | 4 | 50 W | 0.08-80 mW |
| 850 nm | IRED | 8 | 37.5 mW | 300 mW |
| 630 nm | LED | 8 | 25 mW | 200 mW |
| n/a | MAGNET | 8 | 13 mT | 110 mT |

Patient selection involved intubated and mechanically ventilated critically ill COVID-19 patients in the intensive care unit. The trial aimed to demonstrate that daily application of the photoceutical (until death or discharge) can reduce atrophy of the primary inspiratory muscles (identified to be the diaphragm, the sternocleidomastoid muscles, and the scalene muscles). By reducing the atrophy of the primary inspiratory muscles, the health status of such patients can be improved, for example by (1) preserving respiratory function by preventing atrophy of the primary ventilation muscles, minimizing muscle weakness and fatigue, (2) improving parameters of pulmonary ventilation, (3) shortening the duration of mechanical ventilation, and (4) shortening the length of ICU and hospital stays. Daily application of the photoceutical may also boost immune system function, reduce levels of infection and inflammation, prevent sepsis, and minimize symptoms of post-intensive care syndrome.

Thirty (30) patients participated in the trial: fifteen (15) received a placebo, while fifteen (15) received the photoceutical. For each group, the treatment protocol consisted of, until discharge or death, irradiating the diaphragm muscle (3 sites bilaterally on the abdomen) and the sternocleidomastoid and scalene muscles (1 site bilaterally on the neck) for 60 seconds per site with the photoceutical 1× daily with a total dose of 31.5 J per site (19.2 J of infrared light from IREDs, 12 J of red light from red LEDs, 0.3 J of super pulsed light from super pulsed lasers, and exposure to the magnetic field of 110 mT). At all sites, the administration was transcutaneous. The total dose for all 8 sites was 252 J.

Figure 7:
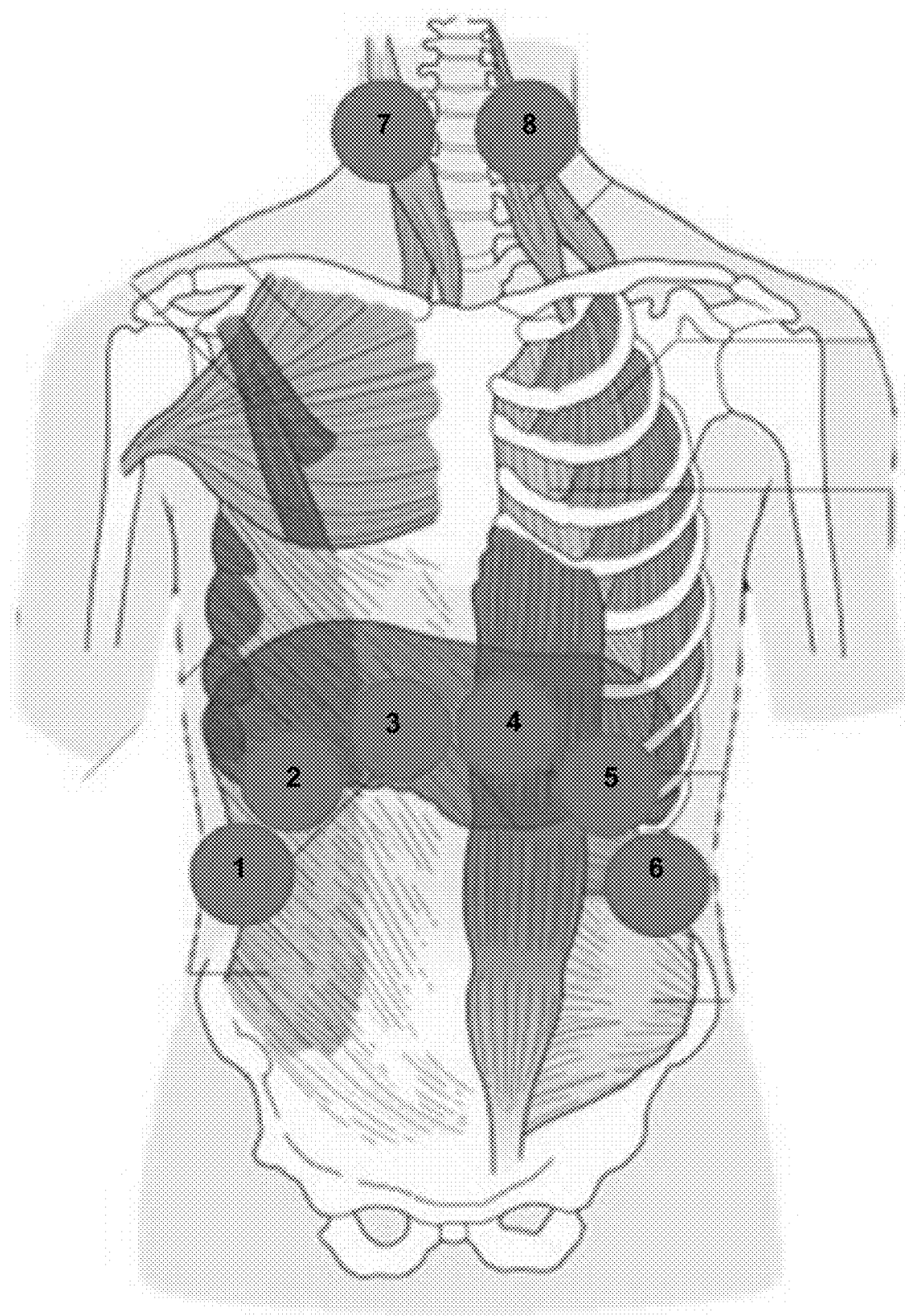
FIG. 7 is a diagram of a patient's inspiratory musculature and the eight locations for delivery of the photoceutical.

The sites are shown in FIG. 7. The first 6 sites cover the abdomen and numbered in sequence from 1-6. An important consideration with regard to the first 6 sites is that the photoceutical should not be delivered to the chest or ribs, so the MR5Active Pro LaserShower should not be placed on the chest or ribs. The diaphragm is recessed under the ribcage, so the light aperture of the MR5Active Pro LaserShower must be angled (from 10 degrees to 50 degrees) by depressing the edge furthest from the costal cartilage into the abdominal wall (FIG. 8) to improve delivery of the light energy to the muscle. The angle allowed light to be directed under the ribcage at the left or right domes of the diaphragm. Pressure on the xiphoid process (the cartilaginous section at the lower end of the sternum, which is not attached to any ribs, and gradually ossifies during adult life) was avoided for all sites because pressure can cause the xiphoid process to break off, resulting in punctures of the diaphragm or even the liver.

Figure 8:
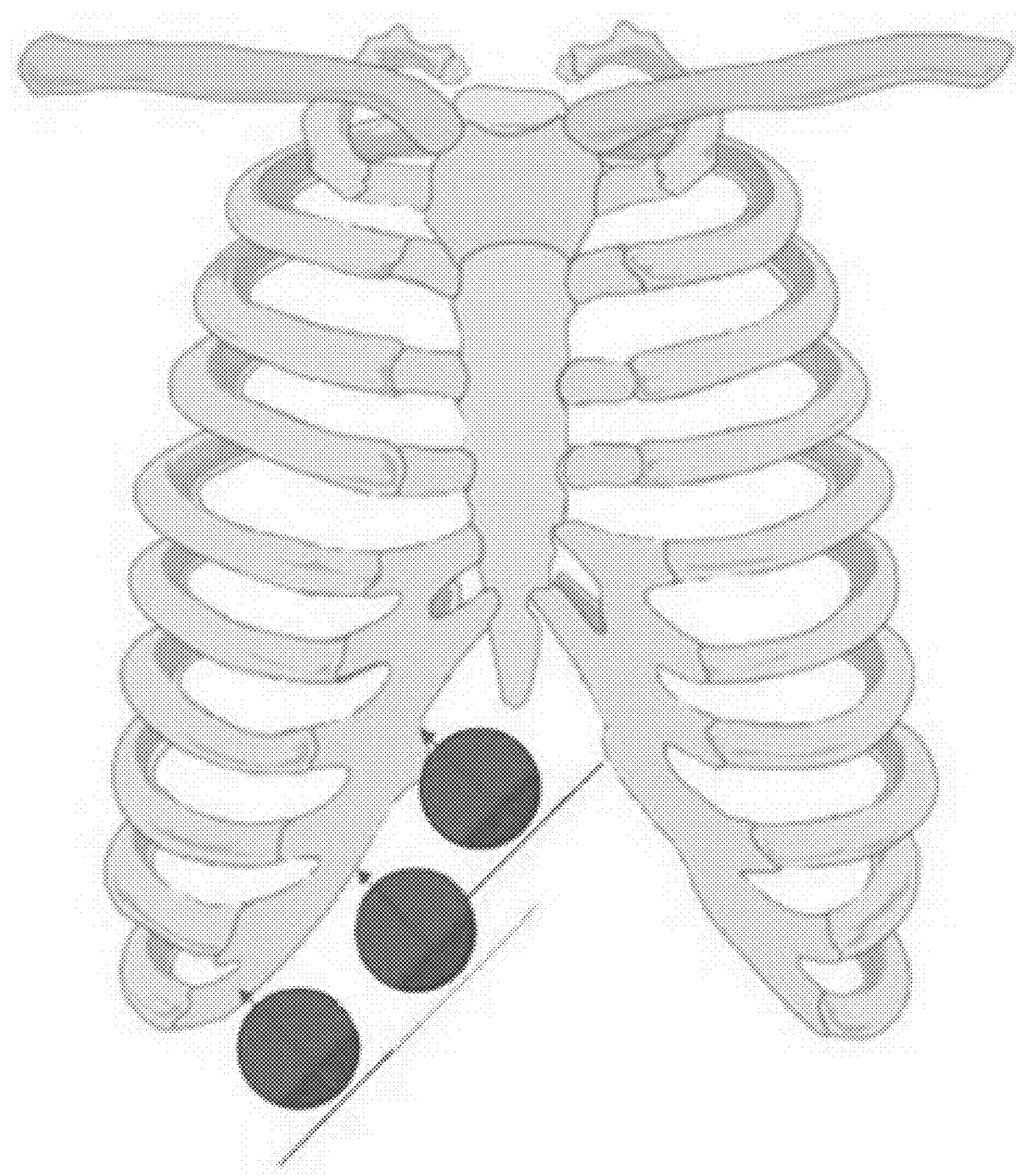
FIG. 8 is a diagram of a portion of the eight locations for delivery of the photoceutical showing how the photoceutical medical device is angled to deliver the photoceutical to the patient's diaphragm.

In FIG. 8, the edge of the light aperture of the MR5Active Pro LaserShower that forms a perpendicular angle and is the farthest away from the costal cartilage landmark (bottom area of circle) was depressed at the angles noted below.

a. Location 1: right 10$^{th}$ rib at the costal cartilage junction, aperture angle is 30' b. Location 2: right 8$^{th}$ rib at the costal cartilage junction, aperture angle is 20' c. Location 3: right 7$^{th}$ rib at the costal cartilage junction, aperture angle is 10' d. Location 4: left 10$^{th}$ rib at the costal cartilage junction, aperture angle is 30' e. Location 5: left 8$^{th}$ rib at the costal cartilage junction, aperture angle is 20' f. Location 6: left 7$^{th}$ rib at the costal cartilage junction, aperture angle is 10'

The final two sites cover the neck, labeled in sequence 7 and 8. Site 7 was at the right body of the sternocleidomastoid, while site 8 was at the left body of the sternocleidomastoid. The light aperture of the MR5Active Pro LaserShower need not be angled for delivery of the dose to sites 7 and 8.

At each site, the treatment was started by pressing the START icon on the MR5Active Pro LaserShower. The treatment was delivered for 60 seconds, then concluded. The MR5Active Pro LaserShower was powered off by pressing and holding the START/STOP icon.

Patients allocated to active group (receiving the photoceutical, referred to as PhotoXyl in some figures) increased diaphragm thickness at the assessment performed at day 10 and at endpoint assessment compared to patients allocated to the placebo group. The preservation and improvement of diaphragm thickness led to a better ventilation/perfusion rate. Therefore, these improvements possibly led to decreased inflammation and infection (CRP) helping the immune response (lymphocytes) of these patients. These findings suggest that the preservation of the main respiratory muscle may trigger a cascade of positive effects, improving the clinical condition of the patients.

Further evaluation of the ventilatory outcomes demonstrated that the photoceutical was able to decrease the FiO2 at endpoint assessment and increased PO2/FiO2 compared to the placebo group. The photoceutical was able to improve some ventilatory parameters, as well as inflammatory and infectious process, and immune response in patients with severe COVID-19 requiring mechanical ventilation. CRP is an acute-phase protein responsible for the clearance of pathogens through the complement system and enhanced phagocytosis. A positive correlation between CRP concentrations with the lung lesion in COVID-19 infected patients has been demonstrated.

Figure 9:
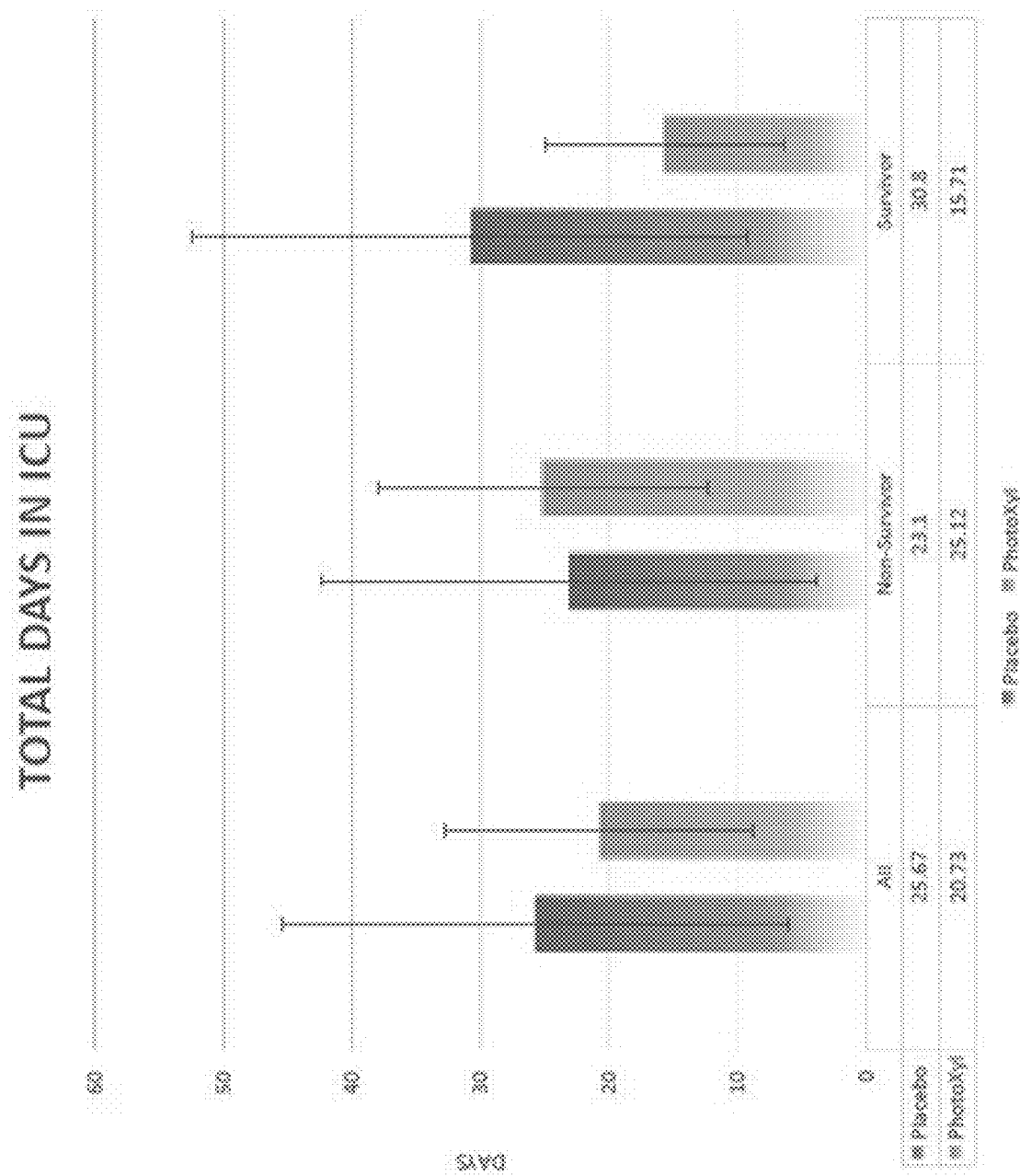
FIG. 9 is a graph showing the total days in the ICU for placebo and photoceutical (PhotoXyl) recipients.
Figure 10:
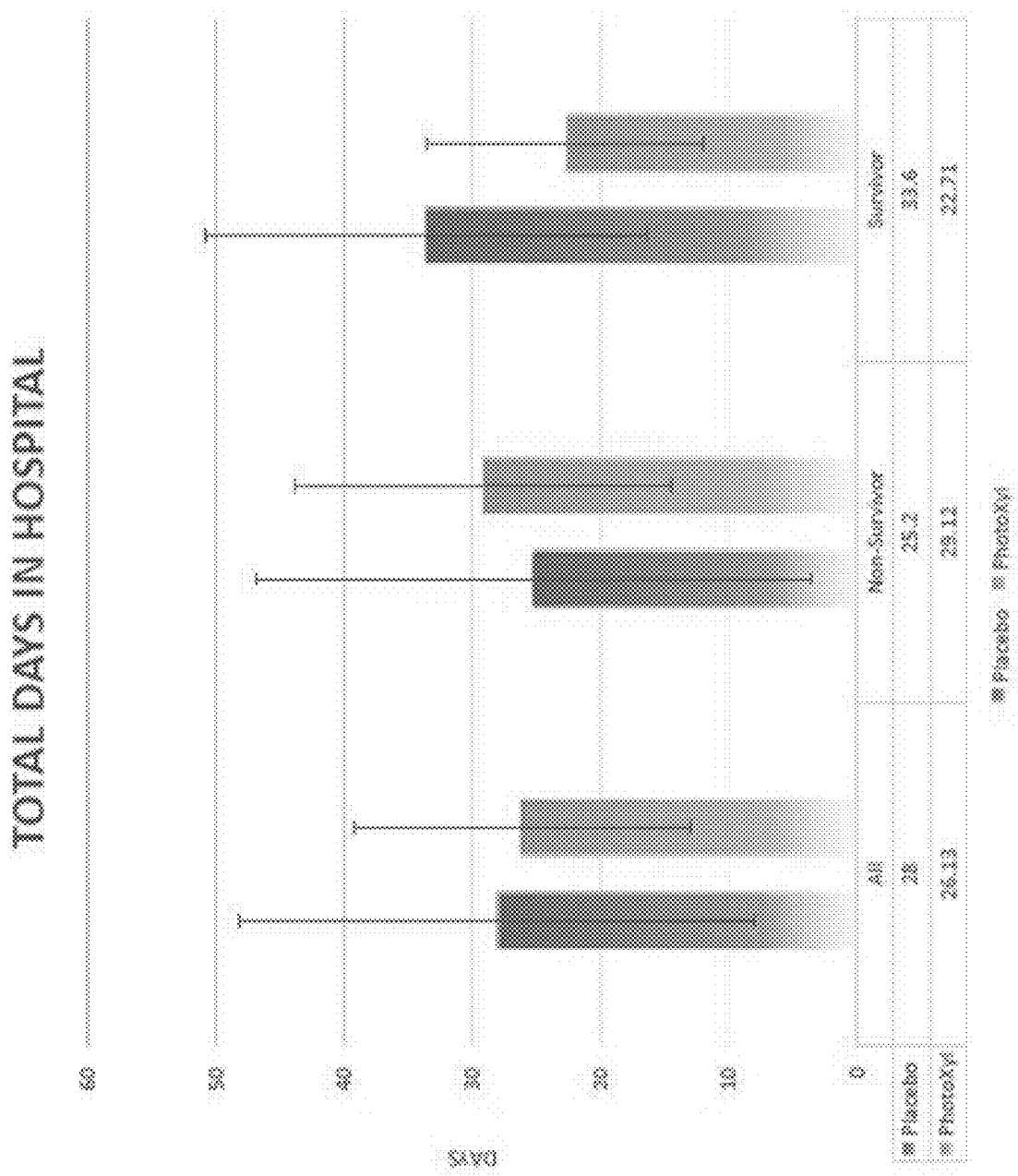
FIG. 10 is a graph showing the total days in the hospital for placebo and photoceutical (PhotoXyl) recipients.
Figure 11:
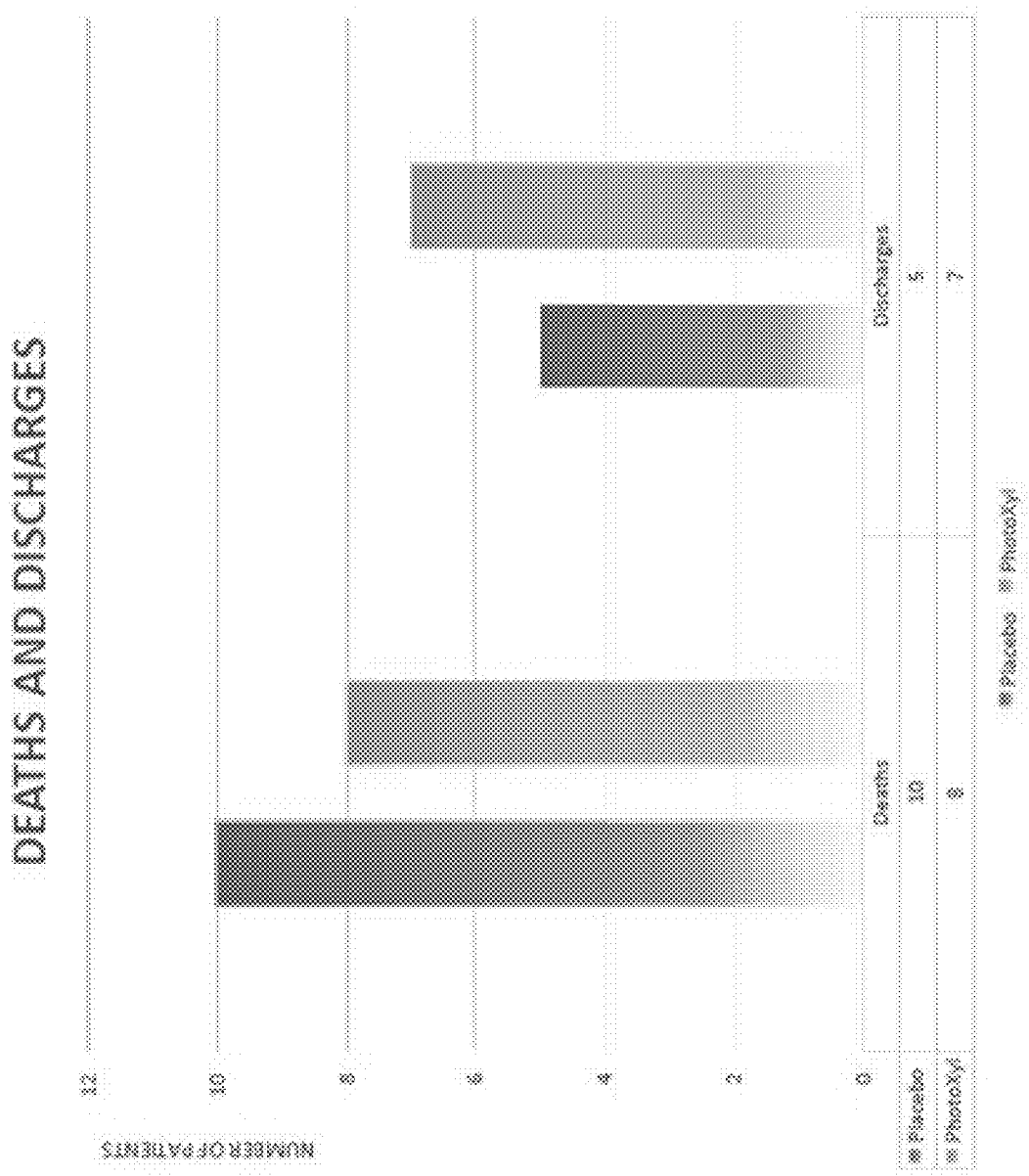
FIG. 11 is a graph showing the number of deaths and discharges for placebo and photoceutical (PhotoXyl) recipients.

Patients in the photoceutical group had shorter length of stay in the ICU (FIG. 9) and the hospital (FIG. 10), considering both all patients and only the survivors. Therefore, these findings suggest that treatment with the photoceutical may reduce the burden caused in the hospital and health systems, and the use of scarce health care resources during the COVID-19 pandemic. In addition, the number of deaths in the photoceutical group was smaller than in the placebo group and the number of discharges higher (FIG. 11). Additionally, the photoceutical decreased intubation time/need by 18% and decreased the length/time of mechanical ventilation by 23%.

Figure 12:
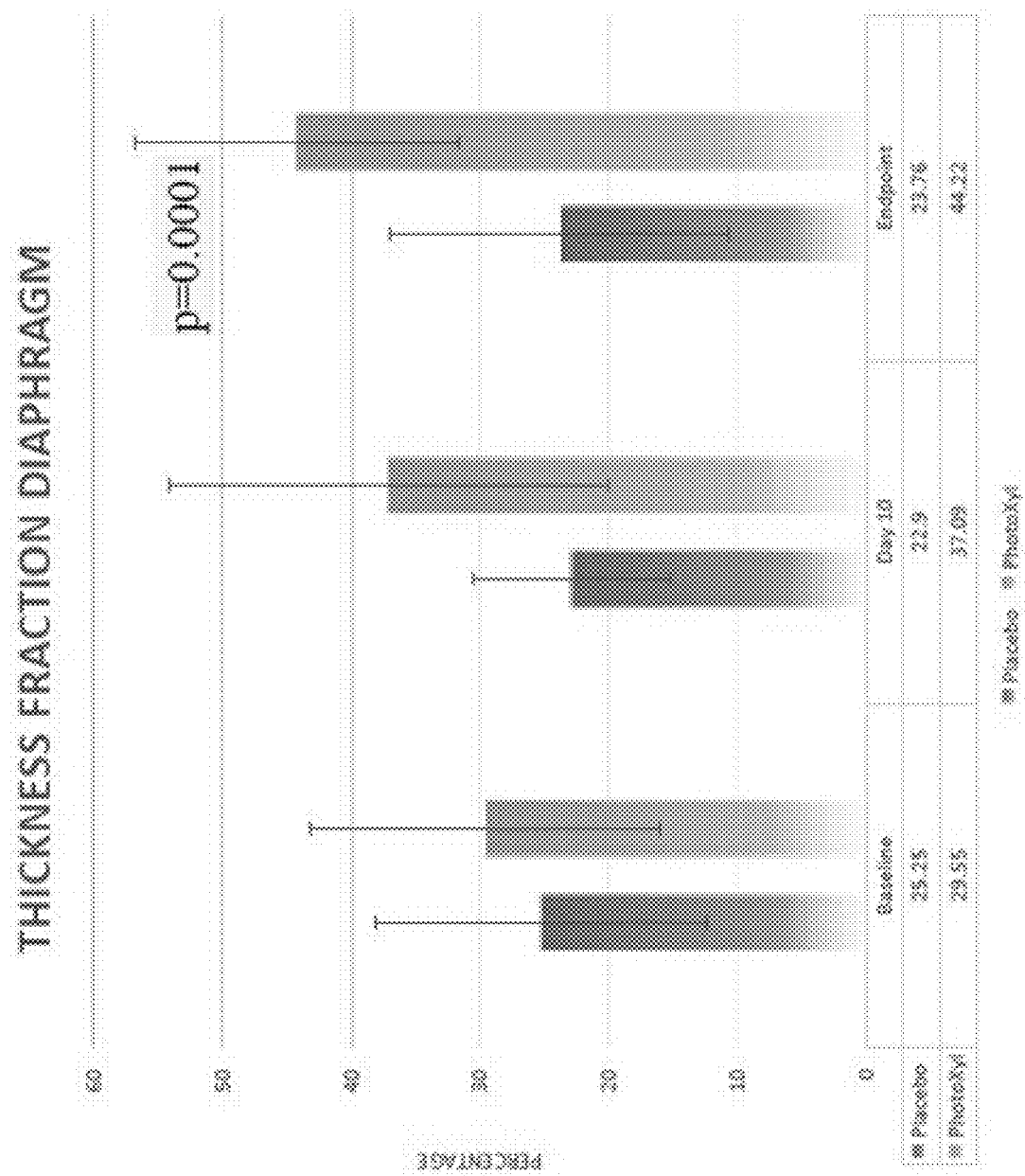
FIG. 12 is a graph showing the thickness fraction of the diaphragm for placebo and photoceutical (PhotoXyl) recipients.
Figure 13:
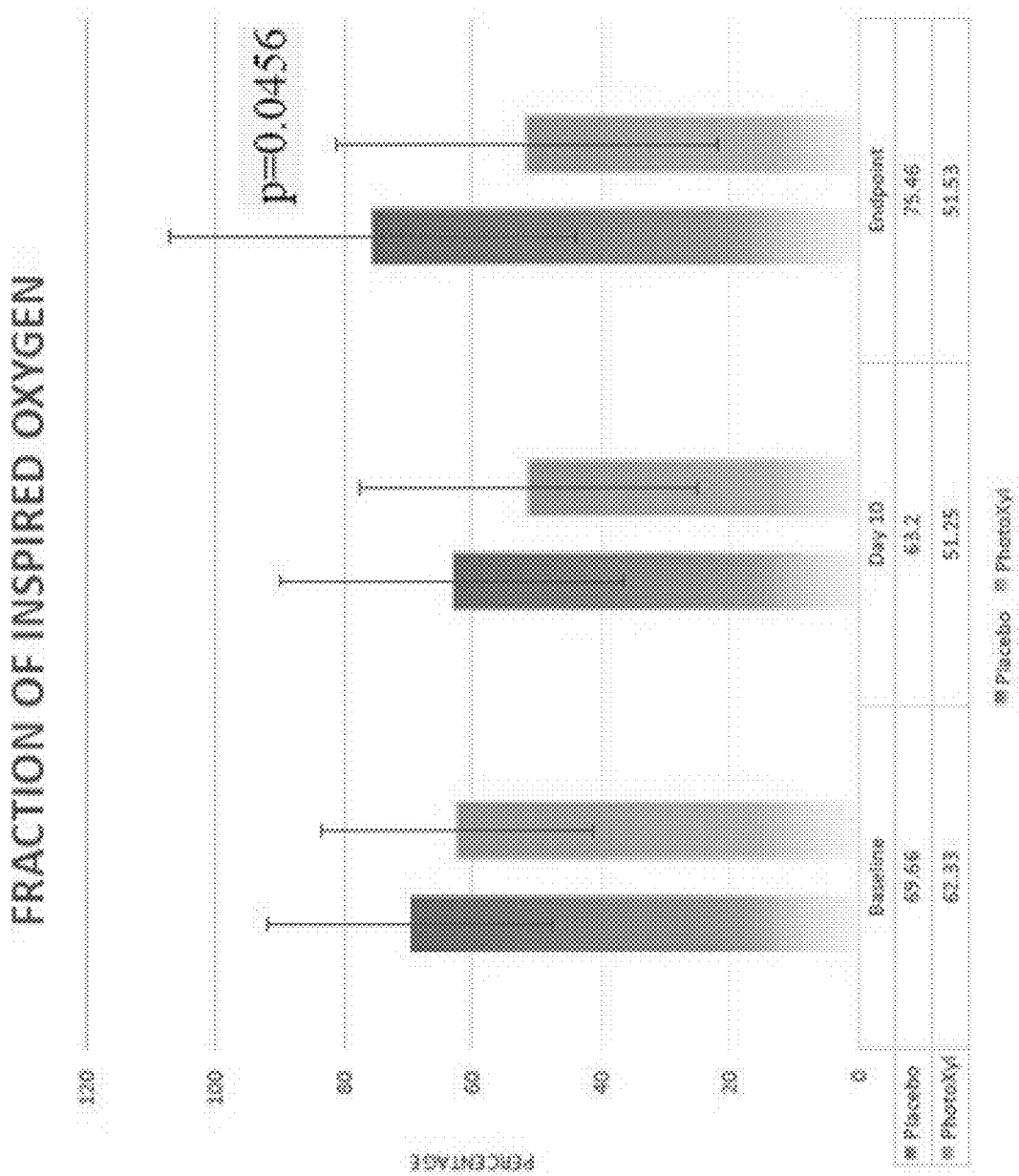
FIG. 13 is a graph showing the fraction of inspired oxygen for placebo and photoceutical (PhotoXyl) recipients.
Figure 14:
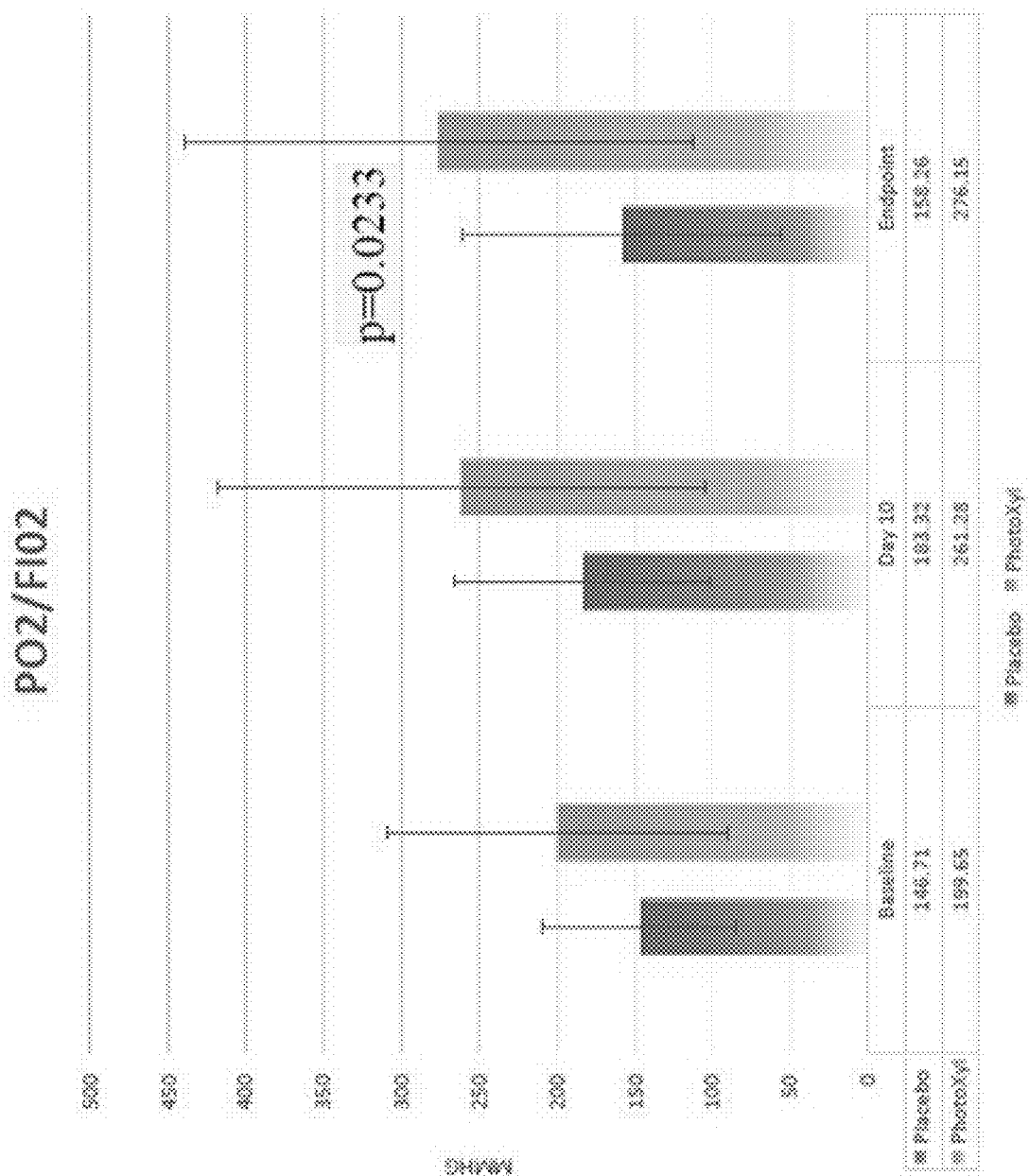
FIG. 14 is a graph showing the $PO_2/FIO_2$ for placebo and photoceutical (PhotoXyl) recipients.
Figure 15:
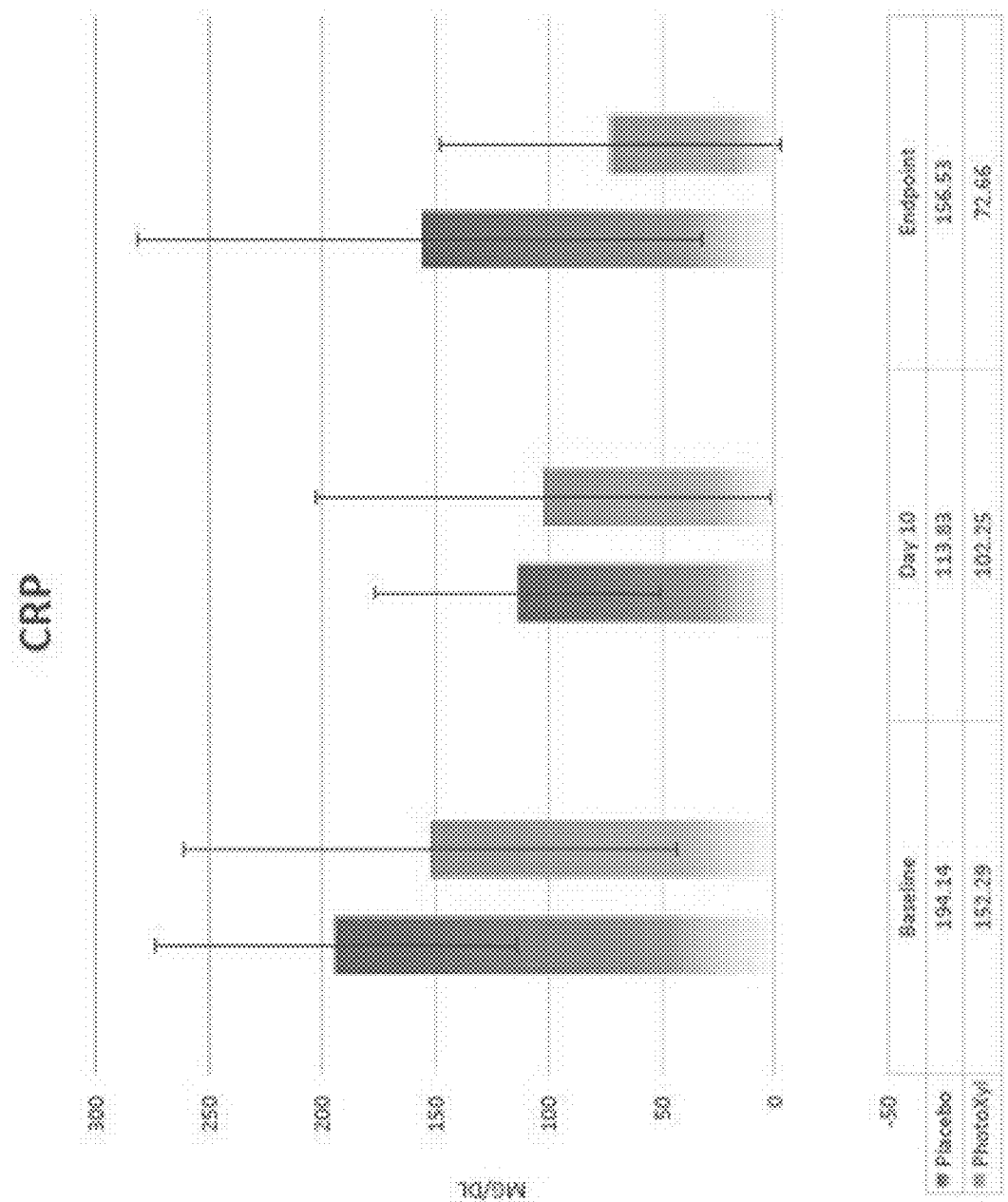
FIG. 15 is a graph showing the CRP for placebo and photoceutical (PhotoXyl) recipients.
Figure 16:
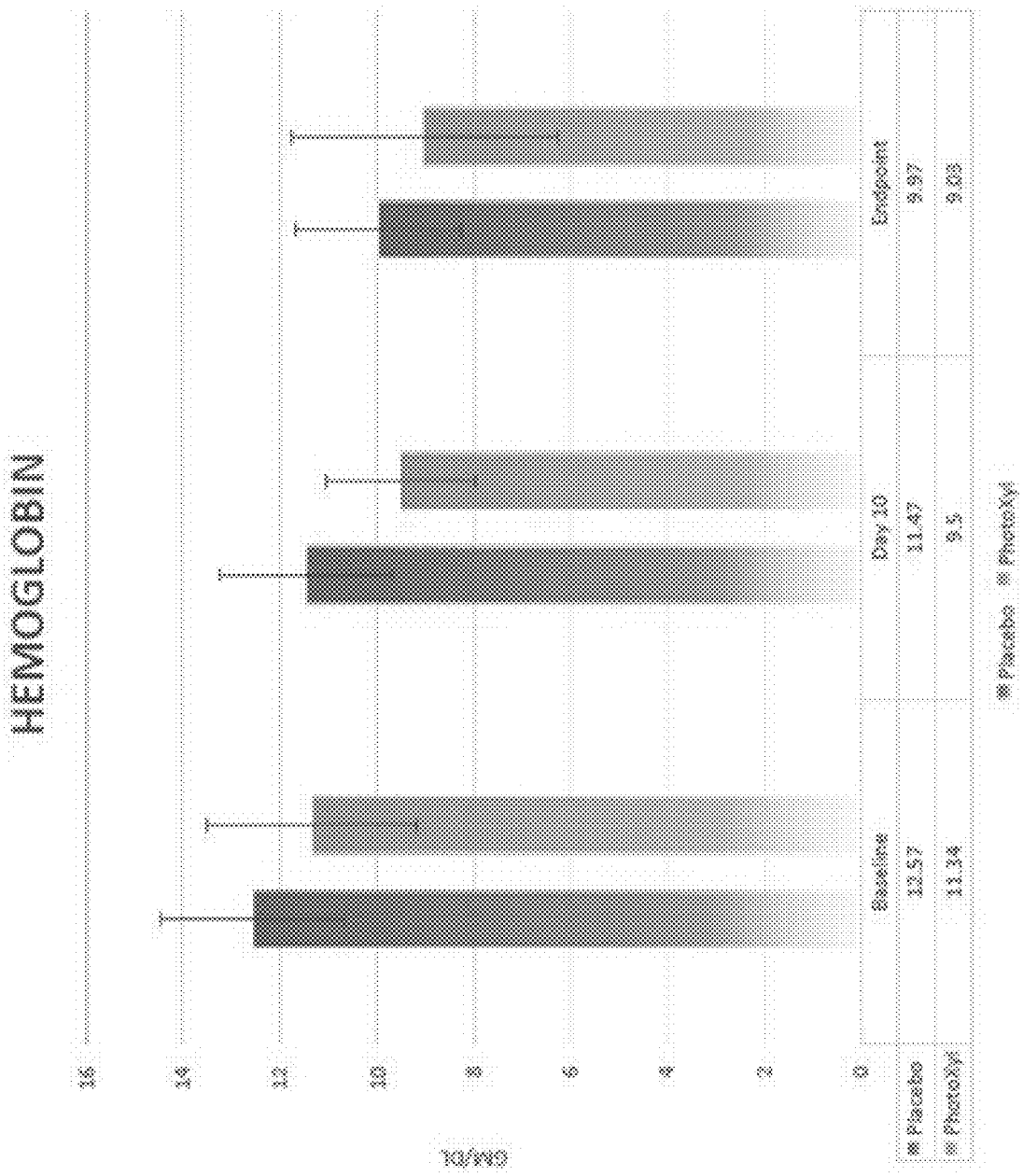
FIG. 16 is a graph showing the hemoglobin for placebo and photoceutical (PhotoXyl) recipients.
Figure 17:
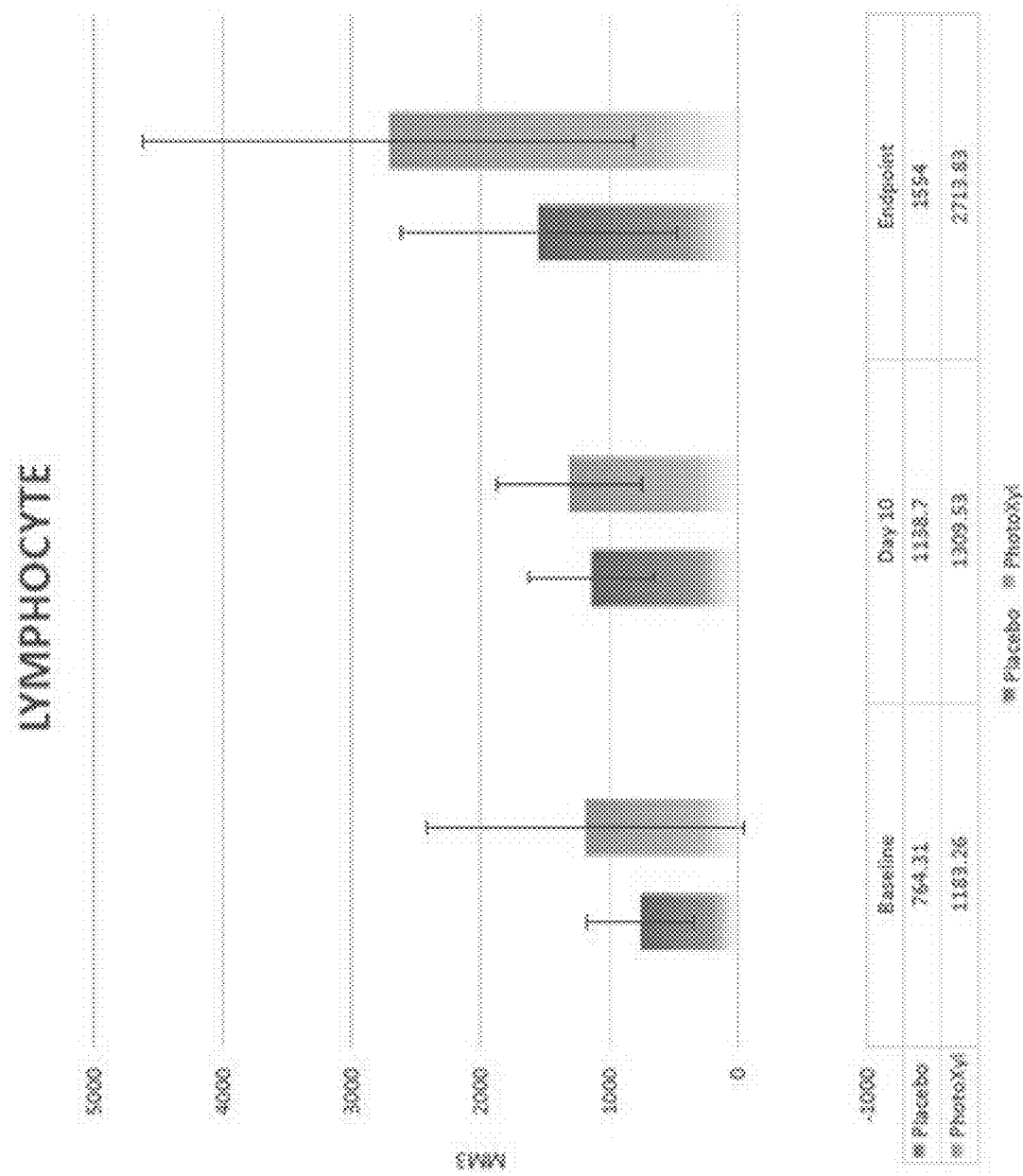
FIG. 17 is a graph showing the lymphocytes for placebo and photoceutical (PhotoXyl) recipients.

The photoceutical increased muscle function of diaphragm (FIG. 12, showing thickness fraction of the diaphragm), improved ventilatory parameters (FIGS. 13, 14), decreased C-reactive protein (CRP) levels (FIG. 15) and hemoglobin count (FIG. 16), and increased lymphocyte count (FIG. 17).

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
 selecting at least two sites on a body of a patient requiring mechanical ventilation for delivery of a light signal to at least one primary inspiratory muscle of the patient by a photoceutical medical device,
 wherein the photoceutical medical device comprises:
  at least one super pulsed laser to provide superpulsed light of a first wavelength,
  at least two non-coherent light sources to provide light of a second wavelength, and
  at least two other non-coherent light sources to provide light of a third wavelength,
  such that the light signal comprises superpulsed light of the first wavelength, light of the second wavelength, and light of the third wavelength; and
 delivering the light signal to the at least one primary inspiratory muscle of the patient by the photoceutical medical device at one of the at least two sites for a first time period from a first start time to a first end time; and
 after the first end time, delivering the light signal to the at least one primary inspiratory muscle of the patient by the photoceutical medical device at another of the at least two sites for a second time period from a second start time to a second end time; and
 wherein the light signal is applied to preserve a respiratory function within the body of the patient requiring mechanical ventilation while on mechanical ventilation.

2. The method of claim 1, wherein the at least one primary inspiratory muscle comprises at least one of a diaphragm, a sternocleidomastoid muscle, and a scalene muscle.

3. The method of claim 1, wherein the patient suffers from severe COVID-19.

4. The method of claim 1, wherein the photoceutical medical device comprises at least two magnetic sources to provide a magnetic signal.

5. The method of claim 1, wherein the first wavelength is between 850 nm and 950 nm, the second wavelength is between 800 nm and 900 nm, and the third wavelength is between 580 nm and 800 nm.

6. The method of claim 1, wherein the photoceutical medical device comprises:
 at least four super pulsed lasers, each configured to provide the superpulsed light of the first wavelength;
 at least eight light sources, each configured to provide the light of the second wavelength;
 at least eight other light sources, each configured to provide the light of the third wavelength; and
 at least eight magnetic sources to provide a magnetic signal.

7. The method of claim 1, wherein at least one of the at least two sites are on an abdomen of the patient to target a diaphragm of the patient requiring mechanical ventilation, and
 wherein the delivering steps each include angling at least a portion of the photoceutical medical device so that the light signal enters the body of the patient at an angle from 10 degrees to 50 degrees to reach the diaphragm of the patient requiring mechanical ventilation.

8. The method of claim 7, wherein the at least one of the at least two sites on the abdomen of the patient is selected so that the light signal is delivered under a ribcage of the patient requiring mechanical ventilation at a left dome or a right dome of the diaphragm of the patient.

9. The method of claim 1, wherein the preserved respiratory function causes improved ventilation parameters, improved blood oxygenation, improved tissue oxygenation, improved immune response, decreased inflammation, minimized symptoms of post-intensive care syndrome, decreased length of intensive care unit (ICU) stay, reduced length of intubation, reduced length of mechanical ventilation, reduced acute respiratory distress syndrome, maintained muscle morphology, maintained muscle function, reduced infection, reduced inflammation, reduced sepsis, and/or decreased length of hospitalization.

10. The method of claim 1, wherein the selecting further comprises selecting at least six sites on the body of the patient for delivery of the light signal to the at least one primary inspiratory muscle of the patient.

11. The method of claim 10, wherein the delivering steps are completed sequentially by placing the photoceutical medical device at an edge of costal cartilage while avoiding the xiphoid process at one or more of the at least six sites.

12. The method of claim 1, wherein the selecting further comprises:
    selecting at least six sites on an abdomen of the patient for delivery of the light signal to the patient's diaphragm; and
    selecting at least two additional sites on a neck of the patient for delivery of the light signal to the patient's sternocleidomastoid and/or scalene muscles.

13. The method of claim 1, wherein the first time period and the second time period each comprises from 30 seconds-300 seconds.

14. The method of claim 1, wherein a dose of 31.5 J is delivered at each of the at least two locations by the photoceutical medical device.

\* \* \* \* \*